United States Patent
Susilo et al.

(10) Patent No.: US 6,303,642 B1
(45) Date of Patent: Oct. 16, 2001

(54) USE OF 2-METHYL-THIAZOLIDINE-2,4-DICARBOXYLIC ACID AS A MUCOLYTIC AGENTS

(75) Inventors: Rudy Susilo, Münsteiferstr. 39, 50937 Köln; Hans Rommelspacher, Berlin, both of (DE); Lidia Wlodek, Krakow (PL)

(73) Assignee: Rudy Susilo, Cologne (DE)

( * ) Notice: Subject to any disclaimer, the term of this patent is extended or adjusted under 35 U.S.C. 154(b) by 0 days.

(21) Appl. No.: 09/380,471

(22) PCT Filed: Feb. 24, 1998

(86) PCT No.: PCT/DE98/00585

§ 371 Date: Nov. 1, 1999

§ 102(e) Date: Nov. 1, 1999

(87) PCT Pub. No.: WO98/38995

PCT Pub. Date: Sep. 11, 1998

(30) Foreign Application Priority Data

Mar. 3, 1997 (DE) ............................................... 197 11 052

(51) Int. Cl.[7] .................................................. A61K 31/425

(52) U.S. Cl. .............................................................. 514/365
(58) Field of Search ............................................. 514/365

(56) References Cited

FOREIGN PATENT DOCUMENTS 2116629  10/1972  (DE) .
0254354   1/1988  (EP) .

OTHER PUBLICATIONS

L. Wlodek et al, "The effect of 2–substitute thiazolidine–4(R)–carboxylic acids on non–protein sulphydryl levels and sulphurtransferase activities in mouse liver and brain.", Biochem. Pharmacol., Bd. 46, Nr. 1, 1993, Seiten 190–193.

L. Wlodek et al, "The antioxidative properties of thiazolidine derivatives.", Pol. J. Pharmacol. Pharm., Bd. 41, Nr. 4, 1989, Seiten 365–375.

*Primary Examiner*—Theodore J. Criares
*Assistant Examiner*—Jennifer Kim
(74) *Attorney, Agent, or Firm*—Wood, Phillips, VanSanten, Clark & Mortimer

(57) ABSTRACT

This invention relates to the use of 2-methyl-thiazolidine-2,4-dicarboxylic acid and/or its physiologically tolerable salts as mucolytic agents.

10 Claims, 5 Drawing Sheets

USE OF 2-METHYL-THIAZOLIDINE-2,4-DICARBOXYLIC ACID AS A MUCOLYTIC AGENTS

Figure 1:
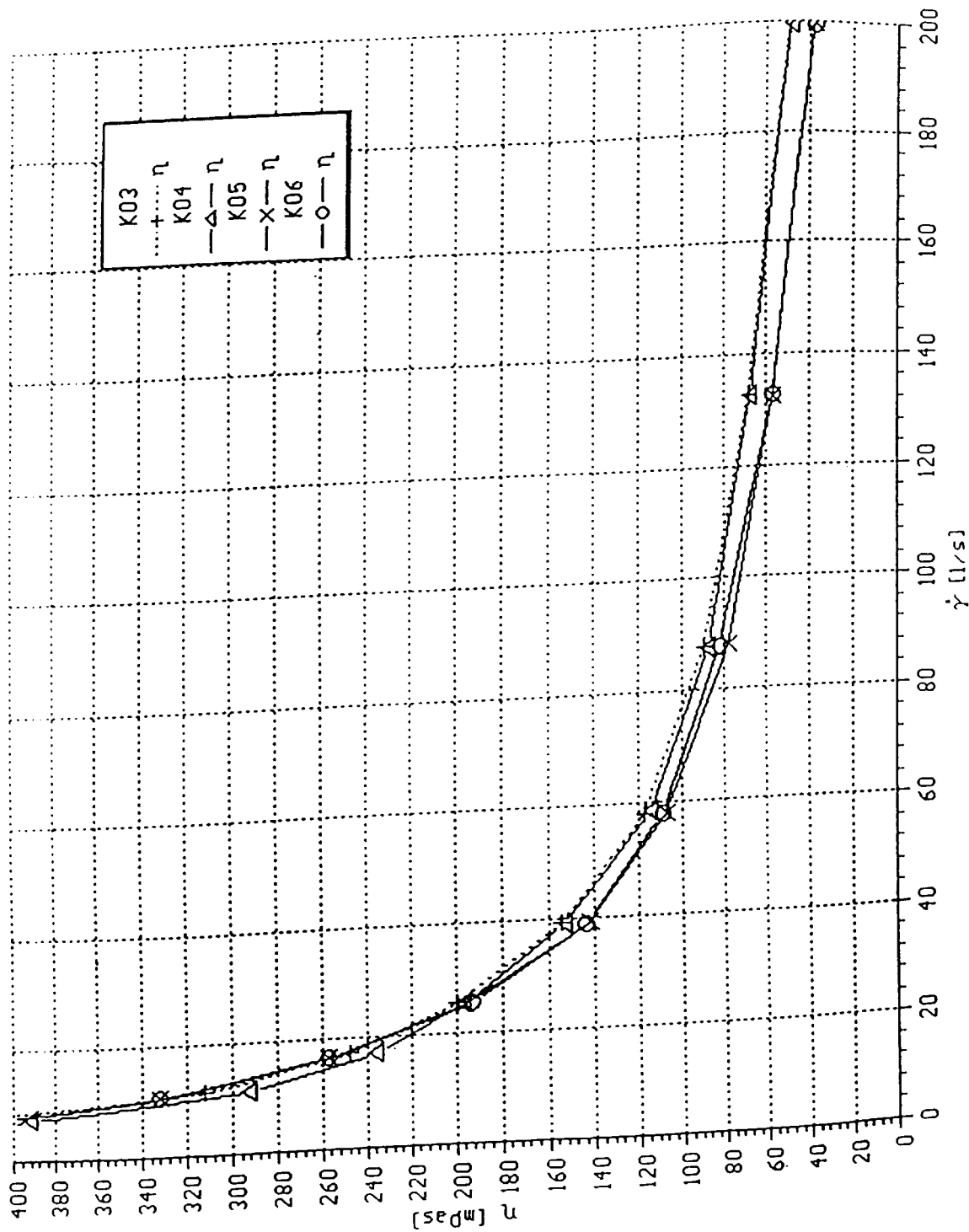

This invention relates to the use of 2-methyl-thiazolidine-2, 4-dicarboxylic acid and/or its physiologically tolerable salts as mucolytic agents. In Germany, N-acetylcysteine and 2-mercaptoethane sulfonate are used as mucolytic agents, N-acetylcysteine being the most common mucolytic agent. Medical indications include diseases of the respiratory tract that are accompanied by intense secretion of a viscid mucus, such as acute and chronic bronchitis, bronchiectasis, asthmoid bronchitis, bronchial asthma, bronchiolitis, and mucoviscidosis.

Two mechanisms are being discussed as regards the mucolytic action of nucleophile N-acetylcysteine. On the one hand, L-cysteine can be released, and on the other it may be that the free sulfhydryl group of the unchanged substance directly splits up the disulfide bridges of the mucoproteins. The consequence is that the mucous components are fractionated, which is a prerequisite for a decrease in viscosity and improved discharge of the mucus.

A minor portion of L-cysteine is released by hydrolysis, the major portion is released by an amino acid N-deacylase which was detected, for example, in the cytosol of hepatic cells (Wlodek, L., Rommelspacher, H., Susilo, R., Radomski, J. and Hefle, G., Biochem. Pharmacol. 46:917–928 (1993)).

It is generally assumed that N-acetylcysteine is a low-toxic pharmaceutical. However, some barely known reports point to the fact that the toxicity risk N-acetylcysteine poses is underestimated (Estrela, J. M., Saez, G. T., Such, L. and Vina, J., Biochem. Pharmacol. 32:3483–3485 (1983), and Vina, J., Romero, F. J., Saez, G. T. and Pallardo, F. V., Experientia 39:164–165 (1983)). Researchers repeatedly tried to find alternatives because of the fact that N-acetyl cysteine can trigger toxic responses. It is absolutely improper to apply L-cysteine itself as this amino acid is highly toxic and causes the death of brain cells (Karlsen, R. L., Grofova, Y., Malthe-Sorensen, D. und Farnum, E., Exp. Brain. Res. 208:167–180 (1981)). This toxicity can be bypassed if a so-called prodrug is applied, i. e. a predecessor pharmaceutical from which the effective amino acid is released in a controlled way inside the body.

The condensation of carbonyl-containing substances with L-cysteine to thiazolidines has been described before (Susilo, R., Rommelspacher, F. and Hoefle, G., J. Neurochem. 52:1793–1800 (1989)). It is important in this context that said thiazolidines form an L-cysteine reservoir from which the amino acid is released as required. An example of a simply structured thiazolidine is the condensation product of formaldehyde and L-cysteine. Metabolites of this substance proved to be neurotoxic, however. The condensation product of acetaldehyde and L-cysteine is not suited as a predecessor pharmaceutical because it is easily decomposed into its components under physiological conditions (Wlodek, L., Rommelspacher, H., Susilo, R., Radomski, J. and Hefle, G., Biochem. Pharmacol. 46:917–928 (1993)).

It is the problem of this invention to provide a physiologically well tolerable substance that acts as a mucolytic agent suitable for treating diseases of the respiratory tract which are accompanied by intense secretion of mucus, and comprises-less side-effects than the substances used as yet that represent the state of the art.

This problem is solved according to the invention by using 2-methyl-thiazolidine-2,4-dicarboxylic acid and/or its physiologically tolerable salts as mucolytic agents.

It was surprisingly found that 2-methyl-thiazolidine-2, 4-dicarboxylic acid or its physiologically tolerable salts are mucolytic agents.

The synthesis of 2-methyl-thiazolidine-2,4-dicarboxylic acid, its use as a hepaprotective agent, and the manufacture of pharmaceuticals in the form of lozenges or ointments containing 2-methyl-thiazolidine-2, 4-dicarboxylic acid are known from DE-OS 21 16 629. Nothing was known as yet about the mucolytic qualities of 2-methyl-thiazolidine-2, 4-dicarboxylic acid and its physiologically tolerable salts.

It is preferred to use 2-methyl-thiazolidine-2, 4-dicarboxylic acid and/or its physiologically tolerable salts for treating diseases of the respiratory tract that are accompanied by intense secretion of mucus.

Use is particularly preferred in the case of diseases of the respiratory tract that are accompanied by intense secretion of a viscid mucus, such as acute and chronic bronchitis, bronchiectasis, asthmoid bronchitis, bronchial asthma, bronchiolitis, and mucoviscidosis.

2-Methyl-thiazolidine-2,4-dicarboxylic acid surprisingly reduces the viscosity of bronchial mucus. Equimolar concentrations of 2-methyl-thiazolidine-2,4-dicarboxylic acid and N-acetylcysteine show a similar efficacy when the mucus is comparatively low-viscous. As previous studies were carried out in phosphate buffer but the SH-group of the thiazolidine derivatives is activated particularly by cytosolic and membrane-bound enzymes (Susilo, R., Rommelspacher, F. and Hoefle, G., J. Neurochem. 52:1793–1800 (1989) and Wlodek, L., Rommelspacher, H., Susilo, R., Radomski, J. and Hefle, G., Biochem. Pharmacol. 46:917–928 (1993)), it may be assumed that the mucolytic activity of 2-methyl-thiazolidine-2, 4-dicarboxylic acid is even more intense in vivo.

It was further found, surprisingly, that 2-methyl-thiazolidine-2, 4-dicarboxylic acid causes a reduction in the formation of free radicals and an increase in the concentration of sulfhydryl groups in the organism. Thus this compound has a cytoprotective and anti-inflammatory effect. This substance therefore is clearly superior to all compounds known as yet, e. g. N-acetylcysteine. The toxic side-effects known from N-acetylcysteine can be considerably reduced by using 2-methyl-thiazolidine-2, 4-dicarboxylic acid as a mucolytic agent.

Pyruvate, a completely harmless physiological substance, is formed as a by-product when L-cysteine is released from 2-methyl-thiazolidine-2,4-dicarboxylic acid. Unlike N-acetylcysteine, 2-methyl-thiazolidine-2,4-dicarboxylic acid is therefore very well tolerated. There are even indications that pyruvate has a protective effect (Rastellini, C., Cicalese, L., Zeevi, A., Mattes, C., Stauko, R. T., Starzl, T. E. and Rao, A. S., Transplant. Proceed. 27:3383–3384 (1995)). Pyruvate is physiologically formed from glucose and is needed in the tricarboxylic acid cycle for producing the cell's energy. It can therefore be expected that a slow enzymatic release of L-cysteine in the cells of the body or in the bronchi has a retarding effect which would give rise to hope for a more lasting efficacy as compared to N-acetylcysteine.

The salts of 2-methyl-thiazolidine-2,4-dicarboxylic acid used according to the invention are produced in a generally known way by reacting 2-methyl-thiazolidine-2, 4-dicarboxylic acid with the respective bases.

Another object of this invention are pharmaceuticals that, in addition to the common substrates and diluents, contain 2-methyl-thiazolidine-2,4-dicarboxylic acid and/or its physiologically tolerable salts as mucolytic agents. The pharmaceuticals of the invention can be designed for oral, rectal, subcutaneous, intravenous or intramuscular administration, or for inhalation.

The pharmaceuticals of the invention are produced in a generally known way using the common solid or liquid substrates or diluents and the commonly used adjuvants of pharmaceutical engineering, their dosage depending on the intended application. Preferred preparations are forms of application suitable for oral administration or for inhalation. Such forms of application include tablets, film tablets, lozenges, capsules, pills, powder, solutions or suspensions, depot systems, or solutions for inhalation.

Parenteral preparations such as injection solutions can also be taken into consideration, of course. Another example of suitable preparations is suppositories.

The respective tablets can be produced, for example, by intermixing the active ingredient with known adjuvants, e. g. inert diluents such as dextrose, sugar, sorbitol, mannite, polyvinylpyrrolidone, blasting agents such as corn starch or alginic acid, binding agents such as starch or gelatin, lubricants such as magnesium stearate or talc and/or agents for producing a depot effect such as carboxyl polymethylene, carboxylmethyl cellulose, cellulose acetate phthalate, or polyvinyl acetate. The tablets may also consist of multiple layers.

Accordingly, lozenges can be produced by coating the cores produced in a similar way as the tablets with agents that are typically used in lozenge coatings, e. g. polyvinylpyrrolidone or shellac, gum arabic, talc, titanium dioxide, or sugar. The lozenge coating may consist of multiple layers, and the adjuvants listed above for tablets can be used here as well.

Solutions or suspensions with the active agent of the invention may further contain sweetening agents such as saccharin, cyclamate or sugar as well as aromatizers such as vanillin or orange extract. They may further contain suspending agents such as sodium carboxymethyl cellulose or preservatives such as p-hydroxybenzoates. Capsules containing active ingredients can be produced, for example, by mixing the active agent with an inert carrier such as lactose or sorbitol, and encapsulating it in gelatin capsules.

Suitable suppositories can be produced, for example, by intermixing with the respective substrates such as neutral fats or polyethylene glycol or their derivatives.

The following example shall explain the invention in greater detail:

EXAMPLE 1

Mucolytic activity of 2-methyl-thiazolidine-2, 4-dicarboxylic acid.

2-Methyl-thiazolidine-2,4-dicarboxylic acid was synthesized using the known method developed by Schubert (Schubert, M. P., J. Biol. Chem. 114:341–350 (1936)).

Fourteen patient samples were tested. The medical diagnoses were:

cystic fibrosis (n=5)

bronchiectasis (n=2)

chronic, spastic bronchitis (n=7)

Seven out of fourteen patients were given N-acetylcysteine. A waiting period of five hours was observed with these patients before a mucus sample was taken. As the viscosity of the samples varied greatly, the viscosity of an aliquot was determined in a preliminary test, and the samples were diluted to such an extent that the viscosity was below 100 mPa * s at a shear rate of 40 per second. The final concentration of the samples was between 60% and 80% of the initial value.

The viscosimeter used was a RheoStress 100 measuring system (Haake, Karlsruhe). Measuring cones of type C60/1 were used; they have an angle of 1 degree and a radius of 30 mm.

The tests were sometimes carried out using samples of just one person, sometimes the samples of up to six respondents were combined. The aliquots of each person were either mixed with a solvent (sodium phosphate buffer, 50 mM, pH 7.0; control samples), or with 15 mM or 30 mM 2-methyl-thiazolidine-2,4-dicarboxylic acid, or with 15 mM or 30 mM N-acetylcysteine (reference substance). The refrigerated samples were cautiously shaken and incubated in a water bath for 15 minutes at 37° C. Subsequently, viscosity was measured using the viscosimeter.

The results of measurement are listed in Table 1 and shown in FIGS. 1 through 5.

TABLE 1

The effect of mucolytic agents on the viscosity of bronchial mucus

| Sample | Mucolytic concentration (mM) | Viscosity (mPa * s) |
| --- | --- | --- |
| KO-1 | 0 | 150.3 |
| CP-1 | 15 | 134.0 |
| CP-1 | 30 | 108.2 |
| NAC-1 | 15 | 71.2 |
| NAC-1 | 30 | 86.0 |
| KO-2 | 0 | 11.0 |
| CP-2 | 15 | 6.7 |
| CP-2 | 30 | 8.1 |
| NAC-2 | 15 | 7.1 |
| NAC-2 | 30 | 8.8 |

Samples taken from six patients were combined for sample no. 1. The values are mean values of six (control) or four measurements, respectively. The samples obtained with the test substances are generally less viscous than the control samples (p<0.01). Sample no. 2 was taken from a single patient.

KO : control sample

CP : 2-methyl-thiazolidine-2,4-dicarboxylic acid

NAC: N-acetylcysteine

Figure 2:
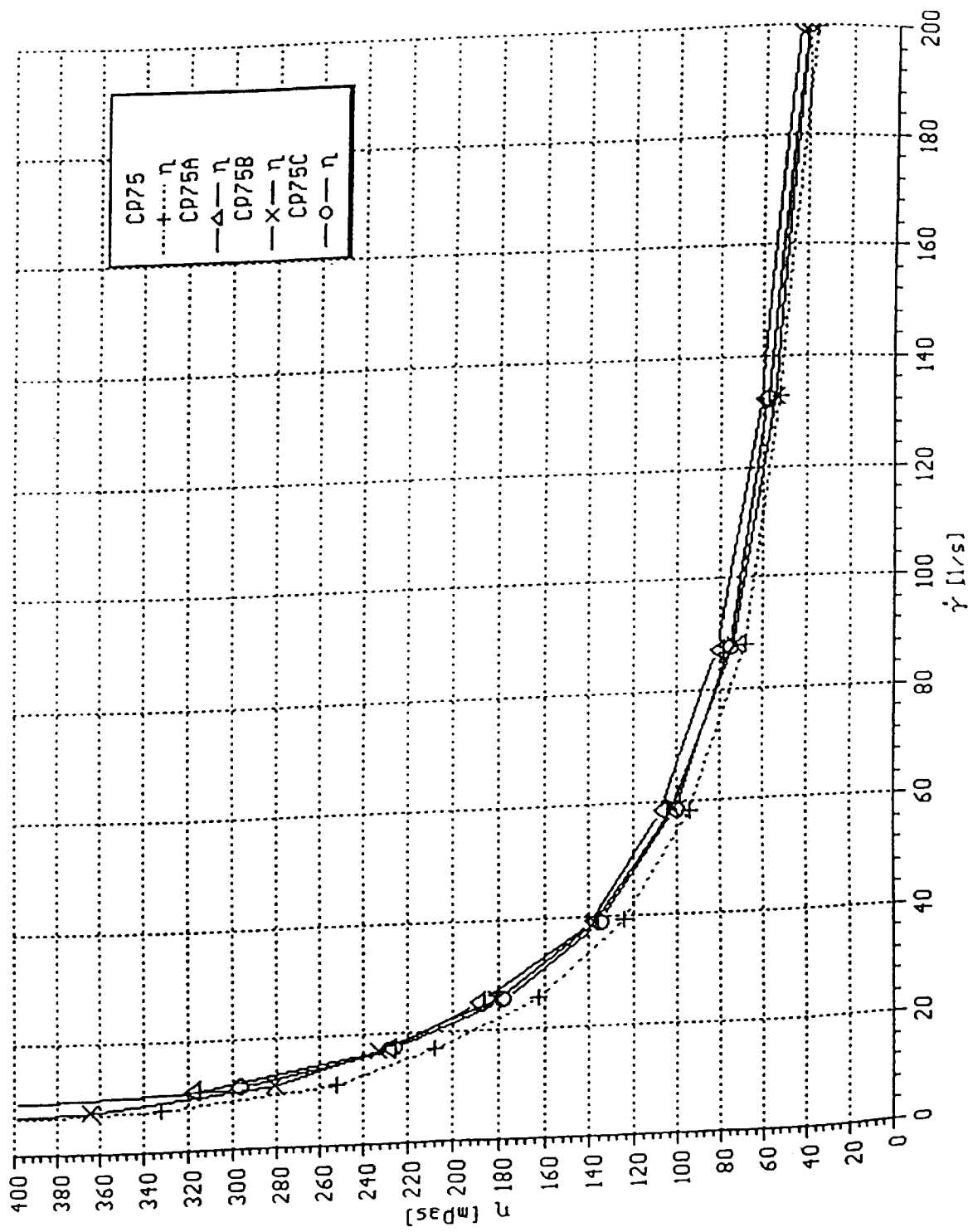
Figure 3:
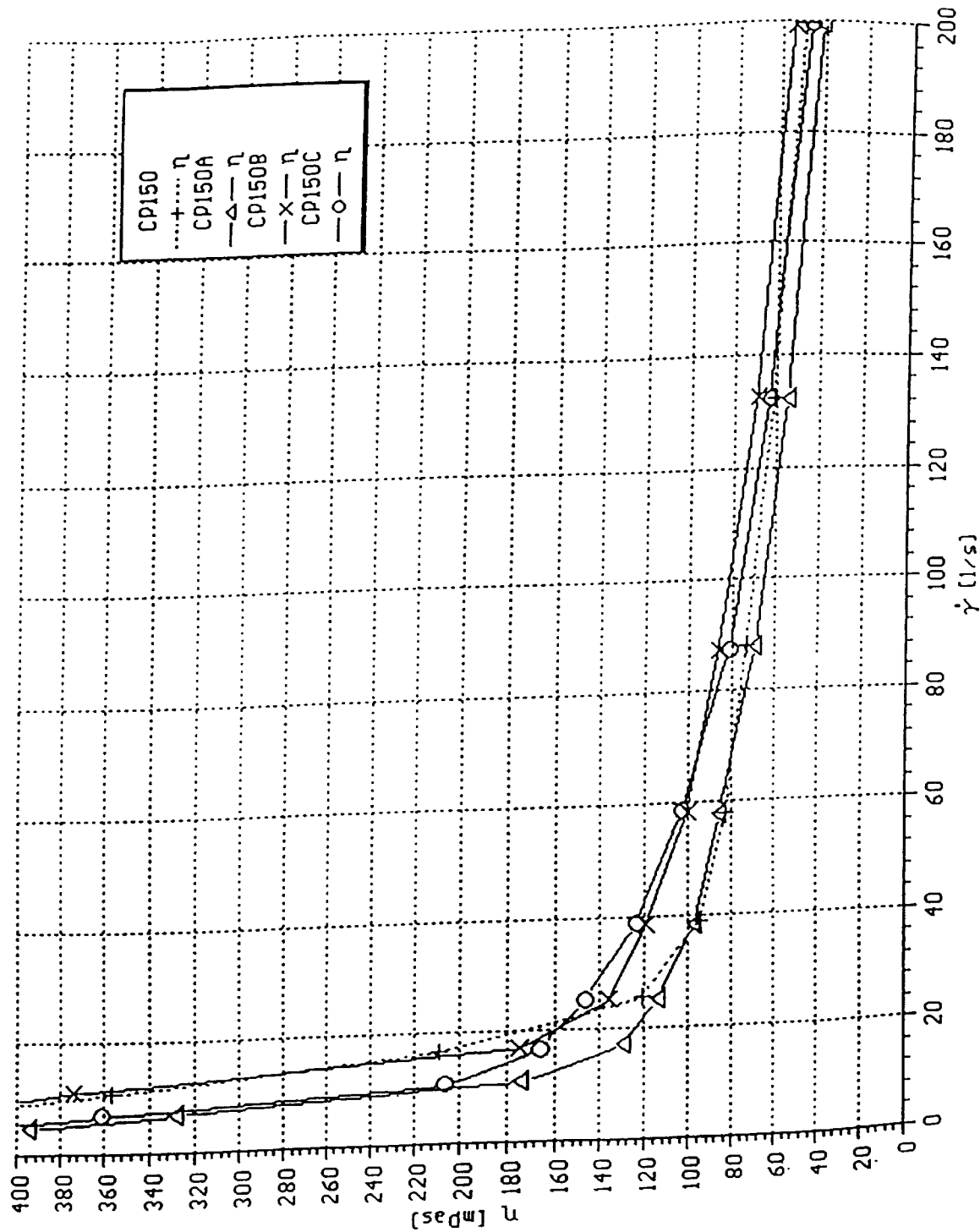
Figure 4:
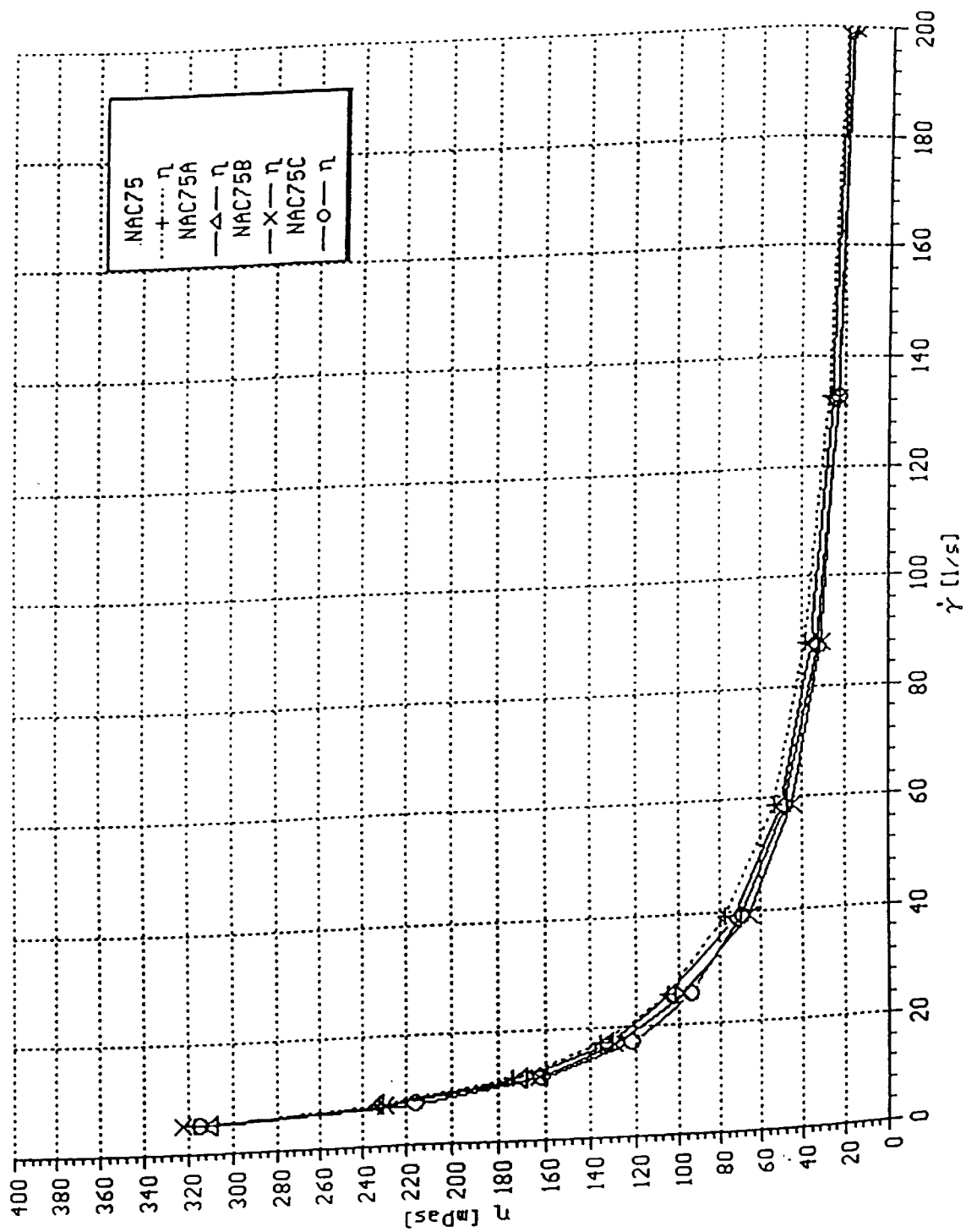
Figure 5:
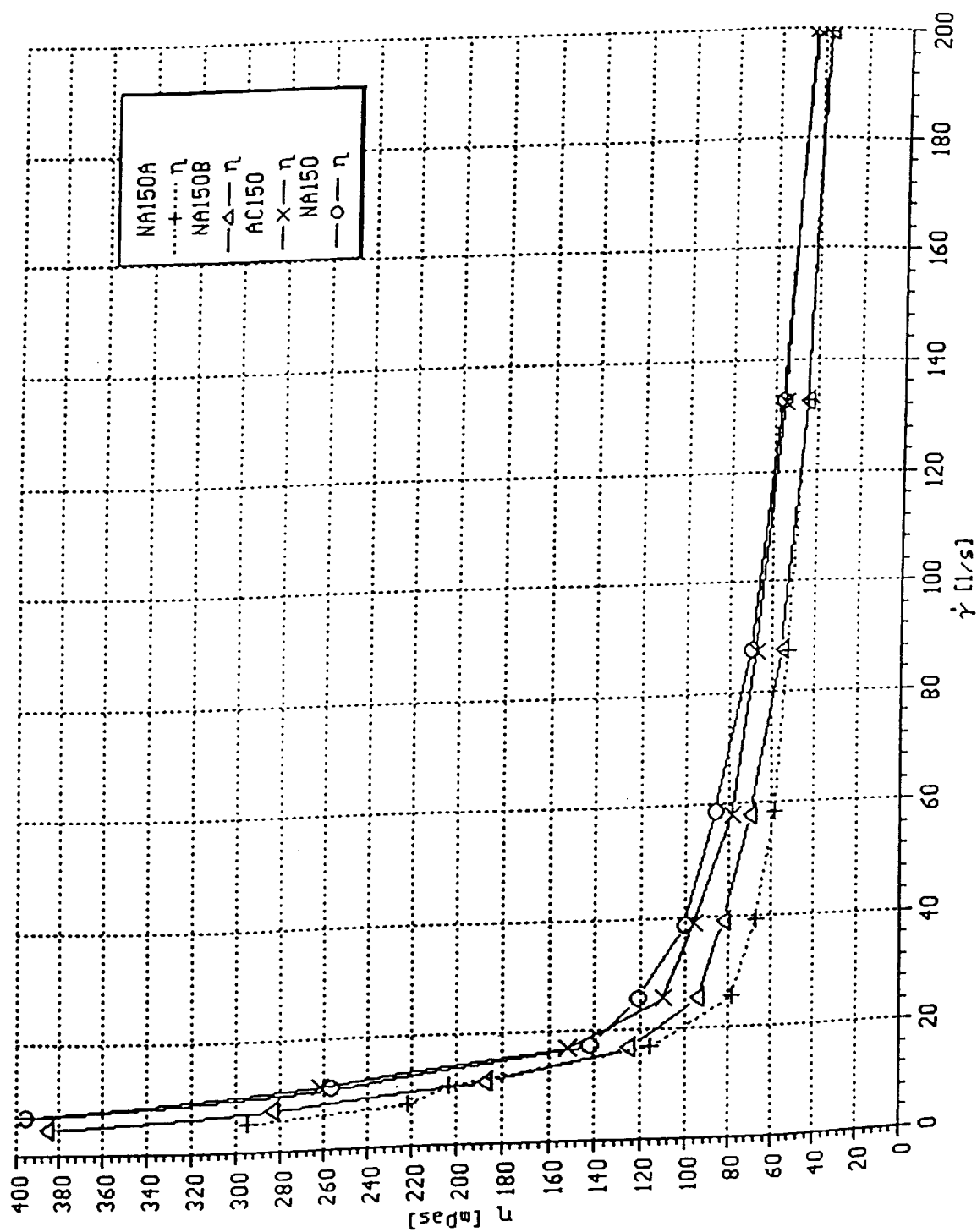

FIGS. 1 through 5 show diagrams wherein the shear rate is outlined on the x-axis and the viscosity is outlined on the y-axis. The value for the control samples (FIG. 1) is on average 150 mPa * s (n=6; only four examples are represented here). 15 mM of CP resulted in a significant decrease in viscosity (FIG. 2; 134 mPa * s). This effect becomes even more obvious when 30 mM of CP are added (FIG. 3; 108 mPa * s). The effects of equimolar concentrations of N-acetylcysteine are more prominent: 71 or 86 mPa * s, respectively (FIGS. 4 and 5). It can be concluded that a maximum effect is reached from as low a concentration as 15 mM of N-acetylcysteine. The efficiency of mucolytic agents apparently strongly depends on the initial viscosity of the sample. It was found using another sample with a considerably lower viscosity (11 mPa * s) that 15 mM of N-acetylcysteine caused a decrease in viscosity to 7.1 mPa * s, and 30 mM of N-acetylcysteine reduced viscosity to 8.8 mPa * s (Tab. 1). This confirms the finding with another sample that 15 mM of N-acetylcysteine will already have a maximum effect. Interestingly, it was observed that 15 mM of the thiazolidine derivative caused a similar decrease in viscosity (6.7 mPa * s), and that this effect could not be enhanced by doubling the concentration (30 mM; 8.1 mPa * s).

BRIEF DESCRIPTION OF THE DIAGRAMS

FIG. 1:

Viscosity of four control samples (K03 to K06). The shear rate (γ) is outlined on the x-axis, the viscosity (η) is outlined on the y-axis.

FIG. 2:

Viscosity of four samples (CP75, CP75A, CP75B, and CP75C) from the same pool as in FIG. 1 that contain a concentration of 15 mM of 2-methyl-thiazolidine-2, 4-dicarboxylic acid (CP). The shear rate (γ) is outlined on the x-axis, the viscosity (η) is outlined on the y-axis.

FIG. 3:

Viscosity of four samples (CP150, CP150A, CP150B and CP150C) from the same pool as in FIG. 1 that contain a concentration of 30 mM of 2-methyl-thiazolidine-2, 4-dicarboxylic acid (CP). The shear rate (γ) is outlined on the x-axis, the viscosity (η) is outlined on the y-axis.

FIG. 4:

Viscosity of four samples (NAC75, NAC75A, NAC75B, and NAC75C) from the same pool as in FIG. 1 that contain a concentration of 15 mM of N-acetylcysteine (NAC). The shear rate (γ) is outlined on the x-axis, the viscosity (η) is outlined on the y-axis.

FIG. 5:

Viscosity of four samples (NAC150, NAC150A, NAC150B, and NAC150C) from the same pool as in FIG. 1 that contain a concentration of 30 mM of N-acetylcysteine (NAC). The shear rate (γ) is outlined on the x-axis, the viscosity (η) is outlined on the y-axis.

We claim:

1. A method of treating a respiratory disorder characterized by a substantial secretion of mucus in a patient, comprising the steps of:

providing a pharmaceutical preparation comprising 2-methyl-thiazolidine-2,4-dicarboxylic acid or its physiologically tolerable salts; and administering said pharmaceutical preparation to a patient with a respiratory disorder characterized by a substantial secretion of mucus.

2. The method of claim 1, wherein said pharmaceutical preparation is administered to a patient with a respiratory disorder selected from the group consisting of acute and chronic bronchitis, bronchiectasis, asthmoid bronchitis, bronchial asthma, bronchiolitis, and mucoviscidosis.

3. The method according to claim 1, wherein said pharmaceutical preparation comprises at least one common substrate and/or at least one adjuvant.

4. The method according to claim 2, wherein said pharmaceutical preparation comprises at least one common substrate and/or at least one adjuvant.

5. The method according to claim 3, wherein said at least one adjuvant is selected from the group consisting of dextrose, sugar, sorbitol, mannite, polyvinylpyrrolidone, corn starch, alginic acid, gelatin, magnesium stearate, carboxyl polymethylene, carboxymethyl cellulose, cellulose acetate phthalate, and polyvinyl acetate.

6. The method according to claim 4, wherein said at least one adjuvant is selected from the group consisting of dextrose, sugar, sorbitol, mannite, polyvinylpyrrolidone, corn starch, alginic acid, gelatin, magnesium stearate, carboxyl polymethylene, carboxymethyl cellulose, cellulose acetate phthalate, and polyvinyl acetate.

7. The method according to claim 1, wherein the step of administering said pharmaceutical preparation further comprises administering said pharmaceutical preparation by a route selected from the group consisting of: an oral route, a rectal route, a subcutaneous route, an intravenous route, an intramuscular route, and an inhalation route.

8. The method according to claim 2, wherein the step of administering said pharmaceutical preparation further comprises administering said pharmaceutical preparation by a route selected from the group consisting of: an oral route, a rectal route, a subcutaneous route, an intravenous route, an intramuscular route, and an inhalation route.

9. The method according to claim 1, wherein said pharmaceutical preparation comprises at least one salt of 2-methyl-thiazolidine-2,4-dicarboxylic acid.

10. The method according to claim 2, wherein said pharmaceutical preparation comprises at least one salt of 2-methyl-thiazolidine-2,4-dicarboxylic acid.

* * * * *